United States Patent
Kominami

(10) Patent No.: US 9,223,030 B2
(45) Date of Patent: Dec. 29, 2015

(54) RADIATION DETECTION EQUIPMENT AND NUCLEAR MEDICINE DIAGNOSIS DEVICE

(75) Inventor: Shinya Kominami, Mito (JP)

(73) Assignee: Hitachi, Ltd., Tokyo (JP)

( * ) Notice: Subject to any disclaimer, the term of this patent is extended or adjusted under 35 U.S.C. 154(b) by 186 days.

(21) Appl. No.: 13/984,602

(22) PCT Filed: Jan. 27, 2012

(86) PCT No.: PCT/JP2012/051743
§ 371 (c)(1),
(2), (4) Date: Aug. 9, 2013

(87) PCT Pub. No.: WO2012/108277
PCT Pub. Date: Aug. 16, 2012

(65) Prior Publication Data
US 2013/0324847 A1    Dec. 5, 2013

(30) Foreign Application Priority Data
Feb. 10, 2011   (JP) .................. 2011-026706

(51) Int. Cl.
*G01T 1/161* (2006.01)
*A61B 6/03* (2006.01)
*A61B 6/02* (2006.01)
*A61B 6/00* (2006.01)
*A61B 6/04* (2006.01)

(52) U.S. Cl.
CPC .............. *G01T 1/1618* (2013.01); *A61B 6/02* (2013.01); *A61B 6/037* (2013.01); *A61B 6/4258* (2013.01); *A61B 6/0407* (2013.01)

(58) Field of Classification Search
CPC   G01T 1/1618; H01L 27/14676; A61B 6/037; A61B 6/02; A61B 6/4258; A61B 6/0407
See application file for complete search history.

(56) References Cited

U.S. PATENT DOCUMENTS

| 4,093,884 A   * | 6/1978 | Dreyfus et al. ............... 310/328 |
| 2006/0138336 A1 | 6/2006 | Seino et al. |
| 2010/0193694 A1* | 8/2010 | Chen et al. ............... 250/370.01 |

FOREIGN PATENT DOCUMENTS

| JP | 2006-184139 A | 7/2006 |
| JP | 2009-156800 A | 7/2009 |

(Continued)

OTHER PUBLICATIONS

Nucl. Instr. and Meth. A, vol. 585 (2008), pp. 102-104.

(Continued)

*Primary Examiner* — David Porta
*Assistant Examiner* — Mindy Vu
(74) *Attorney, Agent, or Firm* — Mattingly & Malur, PC

(57) ABSTRACT

Provided is radiation detection equipment including: a semiconductor radiation detector which has a semiconductor crystal made of thallium bromide; a capacitor which applies a voltage to the semiconductor radiation detector; and at least one DC power source which accumulates positive charges and negative charges in either of electrodes of the capacitor. Herein, a cathode and an anode in the semiconductor radiation detector are formed of at least one kind of a metal selected from gold, platinum and palladium. Further, the DC power source periodically reverses a voltage of accumulating the positive charges and a voltage of accumulating the negative charges in either of the electrodes of the capacitor per interval shorter than 10 min, thereby to apply the resulting voltage thereto.

17 Claims, 7 Drawing Sheets

(56) References Cited

FOREIGN PATENT DOCUMENTS

| | | |
|---|---|---|
| JP | 2009-259859 A | 11/2009 |
| JP | 2009-264813 A | 11/2009 |
| WO | 2011/111467 A1 | 9/2011 |

OTHER PUBLICATIONS

Nucl. Instr. and Meth. A, vol. 607 (2009), pp. 112-115.
IEEE Trans. Nucl. Sci., vol. 56 (2009), pp. 1859-1862.

* cited by examiner

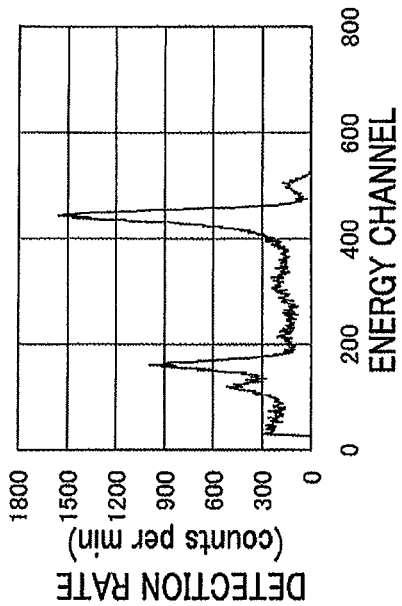
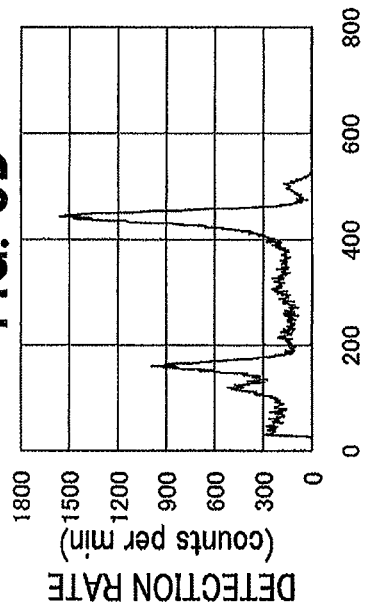
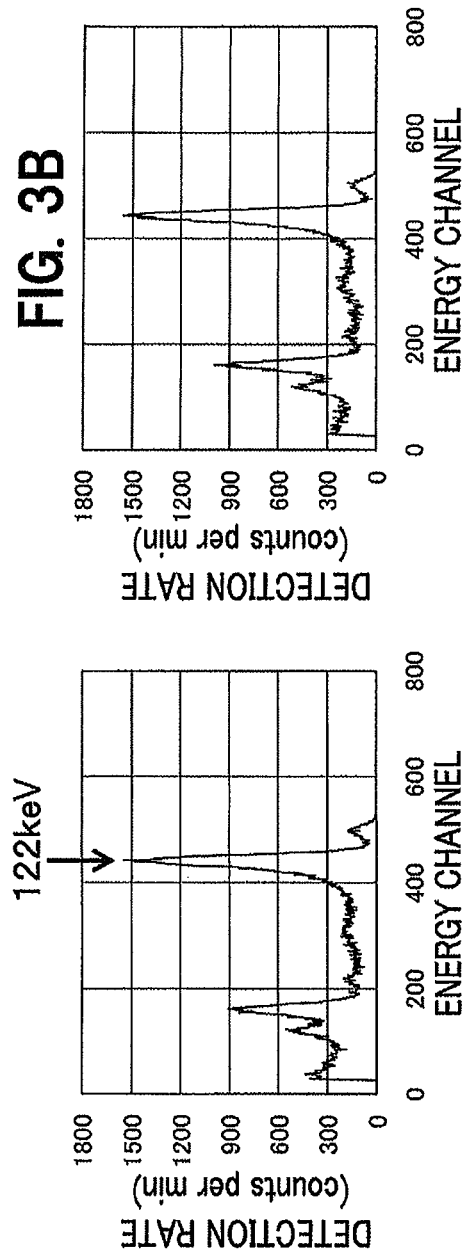
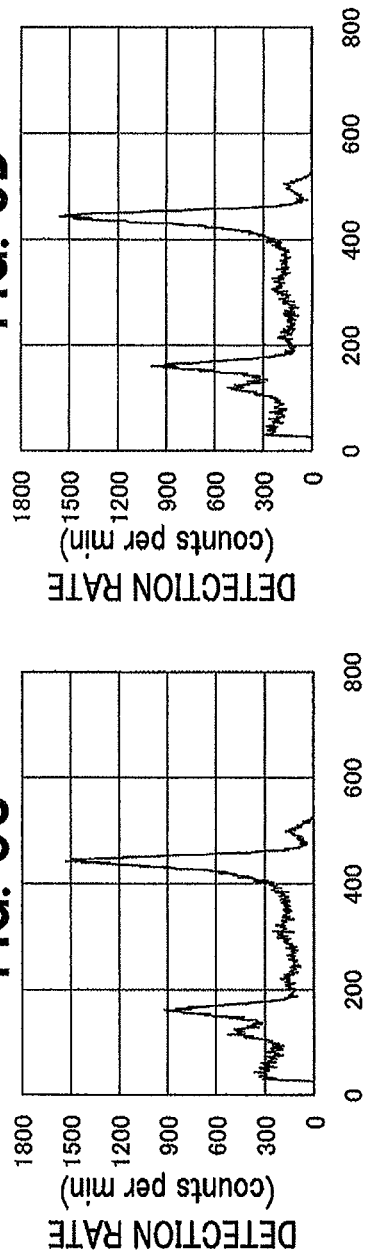

RADIATION DETECTION EQUIPMENT AND NUCLEAR MEDICINE DIAGNOSIS DEVICE

BACKGROUND OF THE INVENTION

1. Field of the Invention

The present invention relates to radiation detection equipment and a nuclear medicine diagnosis device.

2. Description of the Related Art

Recently, a nuclear medicine diagnosis device using radiation detection equipment which detects radiations such as γ rays (or gamma rays) or the like has been widely spread in medical fields. A representative nuclear medicine diagnosis device includes a gamma camera device, imaging equipment for single photon emission computed tomography (SPECT), imaging equipment for positron emission tomography (PET) or the like. Further, a demand for using radiation detection equipment is increasing in a field of homeland security, in which a dosimeter using radiation detection equipment is applied to the dirty bomb counterterrorism.

Conventionally, a radiation detector mounted on the above mentioned radiation detection equipment was produced by combining a scintillator (that is, a device of absorbing radiation energy and subsequently fluorescing) with a photomultiplier tube. However, recently much attention has been paid to a technology using a semiconductor radiation detector comprised of semiconductor crystals of, for example, cadmium telluride (CdTe), cadmium (Cd) zinc (Zn) telluride (Te), gallium arsenide (GaAs), and thallium bromide (TlBr). Such a radiation detector is used for detecting radiations such as γ rays.

A semiconductor radiation detector is a device constructed for converting a charge generated by the interaction between a radiation and a semiconductor crystal into an electrical signal. This feature allows the semiconductor radiation detector to have more efficient performance of converting electrical signals than a detector only using a scintillator. Further, this feature also facilitates the semiconductor radiation detector to be downsized.

Moreover, a semiconductor radiation detector is provided with the semiconductor crystal, a cathode formed on one surface of the semiconductor crystal, and an anode arranged on the other surface of the semiconductor crystal as opposite to the cathode. The application of a direct-current (DC) high voltage between the anode and the cathode enables a signal to be extracted from the cathode or the anode via conversion of a charge generated when a radiation such as an X ray and a γ ray enters a semiconductor crystal.

Among the above described semiconductor crystals, especially a thallium bromide crystal has a larger linear attenuation coefficient due to the photoelectric effect than other semiconductor crystals of cadmium telluride, cadmium zinc telluride, and gallium arsenide or the like. Further, the thallium bromide crystal can realize the same level of γ ray sensitivity as other semiconductor crystals, by using a thin crystal shape thereof.

Accordingly, those features of the thallium bromide crystal enable radiation detection equipment mounting a semiconductor radiation detector comprised of the thallium bromide crystal and a nuclear medicine diagnosis device using the radiation detection equipment to be more downsized than radiation detection equipment mounting other semiconductor radiation detector and a nuclear medicine diagnosis device using such a semiconductor radiation detector.

Further, a price of a thallium bromide crystal is lower than prices of other semiconductor crystals of cadmium telluride, cadmium zinc telluride, and gallium arsenide or the like. This lower price of a thallium bromide crystal allows radiation detection equipment mounting a semiconductor radiation detector comprised of the thallium bromide crystal and a nuclear medicine diagnosis device using the radiation detection equipment to be provided at lower prices than radiation detection equipment mounting other semiconductor radiation detector and a nuclear medicine diagnosis device using such a semiconductor radiation detector.

Conventionally, gold, platinum and palladium or the like have been used for the materials of an anode and a cathode in a thallium bromide based radiation detector. When a bias voltage is applied to a thallium bromide based detector of which anode and cathode are made of gold, platinum and palladium or the like thereby to operate the detector over a long time, positive ions such as $Tl^+$ (or thallium ions) tend to be accumulated near the cathode, and negative ions such as $Br^-$ (or bromide ions) tend to be accumulated near the anode.

Hereby, if such ions are accumulated near the anode and the cathode, that is, if charges are accumulated near the anode and the cathode (namely, if a phenomenon of polarization is caused), a reversed voltage opposite to the applied bias voltage is to be generated, leading to the deterioration of the energy resolution.

However, a recent technology has demonstrated that the usage of thallium layers for causing the formation reactions of a thallium metal and thallium bromide prevents the polarization near a cathode and an anode from occurring, so as to realize the operation stability of the detector. Herein, the thallium layers are respectively inserted between a general cathode and a thallium bromide crystal, and between a general anode and a thallium bromide crystal, in a semiconductor radiation detector comprised of a thallium bromide crystal (for example, see Patent Document 1 and Non-patent Document 1).

That is, an electrochemical reaction of "$Tl^+ + e^- \rightarrow Tl$" occurs near a cathode, and the other electrochemical reaction of "$Br^- + Tl \rightarrow TlBr + e^-$" occurs near an anode. Those reactions may cancel the accumulation of the ions near the cathode and the anode.

Note a term of polarization means a bias phenomenon occurring about a crystal structure, a charge or characteristics, and will be explained more specifically hereinafter.

Further, in addition to the technology of inserting the thallium layers between a cathode and a thallium bromide crystal, and between an anode and a thallium bromide crystal, in a thallium bromide based radiation detector, another technology is also developed.

Such a technology has demonstrated that periodically reversed polarities of the bias voltage applied to a detector for collecting charges enable the detector to be used over a long time. Herein, the periodically reversed polarities are generated per predetermined time in the range from 24 or less hr to 2 or more hr.

The above mentioned technology utilizes a phenomenon that the formation reactions of a thallium metal and thallium bromide are reversible reactions.

PRIOR ART DOCUMENTS

Patent Documents

Patent Document 1: JP 2009-156800

Non-Patent Documents

Non-patent Document 1: Nucl. Instr. and Meth. A, vol. 585 (2008), pp. 102-104

Non-patent Document 2: Nucl. Instr. and Meth. A, vol. 607 (2009), pp. 112-115

Non-patent Document 3: IEEE Trans. Nucl. Sci., vol. 56 (2009), pp. 1859-1862

DISCLOSURE OF INVENTION

Problems to be Solved by the Invention

Here, when a thallium bromide based radiation detector is produced, a step of depositing thallium layers on two counterface surfaces of a thallium bromide crystal may be conducted, in order to stably operate radiation detection equipment mounting the thallium bromide based radiation detector or a nuclear medicine diagnosis device using such radiation detection equipment, over a long time.

When such a step is conducted, a resistance-heated evaporation method or the like is utilized. That is, a thallium layer is deposited by vaporizing a thallium metal in a vacuum vessel to deposit thallium on a surface of the thallium bromide crystal. However, thallium is an acute toxicity substance, which should be handled with extreme care. Further, it should be noted that when thallium is vaporized, apart of thallium is deposited not only on a surface of the thallium bromide crystal but also on a surface inside the vacuum vessel together with a surface inside a vacuum pump used for the vacuum vessel.

In such a case, it is needed to arrange local exhaust ventilation equipment of covering the entire vacuum system, and an abatement system which removes thallium from exhaust gas of a vacuum pump.

Accordingly, when thallium is used for electrodes of a thallium bromide based radiation detector, the manufacturing cost of the detector increases more largely than the case in which metals having low toxicity except for thallium are used. This results in more difficulty in realizing low prices of radiation detection equipment mounting a thallium bromide based radiation detector and a nuclear medicine diagnosis device using the equipment than a radiation detector mounting a metal except for a thallium compound.

On the other hand, it has been found that radiation detection cannot be stably performed, if a thallium layer is not inserted between an electrode of a thallium bromide based detector and a thallium bromide based crystal. Herein, note a cathode and an anode are formed by using gold, platinum or palladium or the like, as conducted in a conventional method, more specifically, by using gold. This drawback is caused because polarization occurs in such a detector, leading to deterioration of the energy spectra thereof, when a bias voltage for collecting charges applied to the detector is continuously applied over a long time and the detection is continued in this condition.

Further, it has been also found that a response of the energy spectrum becomes gradually deteriorating, if a polarity of the bias voltage is reversed after 2 hours detection. More specifically, in such a case, although the response of the energy spectrum is once recovered after reversing the polarity, the response is to gradually deteriorate when the detection is further continued for 2 hours (for example, see Non-patent Document 3).

Therefore, if a cathode and an anode of the thallium bromide based detector are formed by using gold, polarization cannot be prevented from occurring, resulting in difficulty in the stable operation of the detector over a long time. This makes it impossible to stably use the radiation detection equipment mounting a thallium bromide based detector and a nuclear medicine diagnosis device using the radiation detection equipment over a long time.

From the viewpoint of the above mentioned drawbacks, an object of the present invention is to provide inexpensive radiation detection equipment having a stable response performance, and an inexpensive nuclear medicine diagnosis device using the radiation detection equipment.

Means for Solving the Problems

The above mentioned equipment and the devise using the same are constructed as mentioned below, so as to solve the drawbacks and achieve the object of the present invention.

That is, the radiation detection equipment comprises: a semiconductor radiation detector using thallium bromide as a semiconductor crystal; a capacitor of applying a voltage to the semiconductor radiation detector; and at least a DC power source of accumulating positive and negative charges in either of electrodes of the capacitor. Herein, a cathode and an anode of the semiconductor radiation detector are formed of at least one metal selected from gold, platinum and palladium. Further, the DC power source applies a voltage of accumulating positive charges and a voltage of accumulating negative charges to either of the electrodes of the capacitor by periodically reversing the voltage per interval shorter than 10 min.

The above mentioned construction allows polarization to be prevented from occurring and stable radiation detection to be realized, which is achieved without inserting thallium layers between a cathode and a thallium bromide crystal, and between an anode and a thallium bromide crystal, in a thallium bromide based radiation detector.

Effect of the Invention

As mentioned hereinbefore, the present invention is capable of providing inexpensive radiation detection equipment having a stable response performance, and an inexpensive nuclear medicine diagnosis device mounting the inexpensive radiation detection equipment.

BRIEF DESCRIPTION OF DRAWINGS

FIGS. 3A to 3D are schematic diagrams each showing an energy spectrum of the radiation detection equipment in the first embodiment of the present invention. FIG. 3A shows the energy spectrum just after a bias voltage has been applied; FIGS. 3B, 3C and 3D respectively show an energy spectrum in 5, 535 and 540 minutes after a bias voltage has been applied.

FIG. 5A shows response characteristics when a positive bias voltage is first applied; FIG. 5B shows response characteristics when a negative bias voltage is subsequently applied via reversing the polarity; FIG. 5C shows response characteristics when a second positive bias voltage is subsequently applied via reversing the polarity; and FIG. 5D shows response characteristics when a second negative bias voltage is subsequently applied via reversing the polarity.

FIGS. 6A and 6B respectively show the energy spectrum characteristics just after a bias voltage has been applied (FIG. 6A), and in 78 minutes totally after the first application of the bias voltage has been started (FIG. 6B).

EMBODIMENTS FOR CARRYING OUT THE INVENTION

Hereinafter, radiation detection equipment of the present invention and a nuclear medicine diagnosis device mounting the equipment will be described in detail referring to the attached drawings.

First Embodiment of Radiation Detection Equipment

Figure 1:
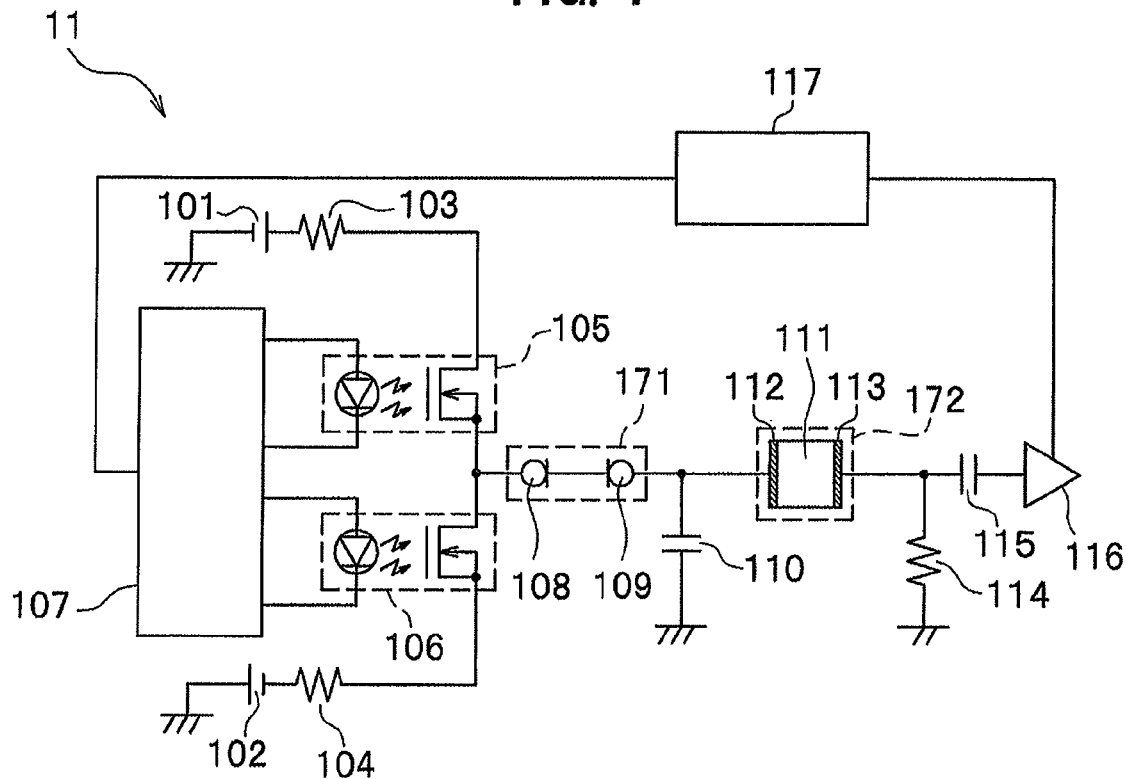
FIG. 1 is a block diagram showing a circuit structure of radiation detection equipment in a first embodiment of the present invention.

FIG. 1 is a bloc diagram showing a circuit structure of the radiation detection equipment in a first embodiment of the present invention. As shown in FIG. 1, radiation detection equipment 11 comprises: a semiconductor radiation detector (hereinafter, simply called a detector) 172 including a semiconductor crystal 111 made of thallium bromide, a first electrode 112 made of gold and a second electrode 113 also made of gold, respectively arranged at opposite surface sides of the semiconductor crystal 111; a smoothing capacitor 110 of applying a voltage to the detector 172; a first DC power source 101 of accumulating positive charges in one of electrodes of the smoothing capacitor 110; and a second DC power source 102 of accumulating negative charges in the other electrode of the smoothing capacitor 110.

The radiation detection equipment 11 further comprises: a first constant regulative diode 108 which is connected by integrating the polarity of the constant-current characteristics so that a current flows from the first DC power source 101 to either of the electrodes of the smoothing capacitor 110; a second constant regulative diode 109 which is connected by integrating the polarity of the constant-current characteristics so that a current flows from either of the electrodes of the smoothing capacitor 110 to the second DC power source 102; a first photoMOS relay 105 connected with a wire which connects the first DC power source 101 and either of the electrodes of the smoothing capacitor 110; and a second photoMOS relay 106 connected with a wire which connects the second DC power source 102 and either of the electrodes of the smoothing capacitor 110.

Further, a protection resistor 103 is arranged between the first DC power source 101 and the first photoMOS relay 105, and a protection resistor 104 is arranged between the second DC power source 102 and the second photoMOS relay 106. Those protection resistors 103 and 104 are provided as resistors for preventing excess currents from flowing.

Herein, a control unit for switches 107 controls opening/closing of the first photoMOS relay 105 and the second photoMOS relay 106.

Further, a bleeder resistor 114 and either of electrodes of a coupling capacitor 115 are connected with an output of a detector 172. An amplifier 116 which amplifies a signal of the detector 172 is connected with the other electrode of the coupling capacitor 115. Moreover, a control unit for polarity integration 117, which controls opening/closing of the photoMOS relays 105 and 106, and timing of reversing a polarity of the amplifier 116, is connected with the control unit for switches 107 and the amplifier 116.

A negative electrode of the first DC power source 101, a positive electrode of the second DC power source 102, the other electrode other than either of the electrodes of the smoothing capacitor 110, and either of the electrodes of the bleeder resistor 114 are respectively connected with ground wires.

Further, the first photoMOS relay 105 and the second photoMOS relay firstly function as relays (or electrical relays). Herein, it should be noted that the relays 105 and 106 have rapid response ability and high reliability because there is no mechanical contact point in the structure so as to prevent malfunction like chattering from occurring. Accordingly, those features allow the photoMOS relays to be used in the present embodiment.

Further, the first constant regulative diode 108 and the second constant regulative diode 109 are connected each other in series so that the polarities of the constant-current characteristics of the diodes are reversed each other. Thus, a current regulator 171 is composed of the diodes 108 and 109. In this construction, presently general constant regulative diodes, which are applied to the first constant regulative diode 108 and the second constant regulative diode 109, generate constant-current characteristics in the structure where a source electrode and a gate electrode of a field effect transistor (FET) are short-circuited.

Hereby, when a reversed voltage is applied to the diodes, the p-n junction formed in the field effect transistor is biased in a forward direction, causing a large current to flow. That is, the current characteristics of the constant regulative diode include a polarity. Therefore, when the first constant regulative diode 108 and the constant regulative diode 109 are connected in series so that the respective polarities in the constant-current characteristics of the diodes are reversed each other, this construction can realize the constant-current characteristics which have no difference in the polarities.

For that reason as mentioned above, the current regulator 171 is constructed so that the first constant regulative diode 108 and the second constant regulative diode 109 are connected in series, whereby the respective polarities of the constant-current characteristics of the diodes are reversed each other. This construction allows the current regulator 171 to have the constant-current characteristics having no difference in the polarities.

If radiations such as γ rays are to be detected by the radiation detection equipment 11, a bias voltage for collecting charges (for example, +500V or −500V) is applied between a first electrode 112 and a second electrode 113 of the detector 172 by the first DC power source 101 or the second DC power source 102 and the smoothing capacitor 110.

When γ rays are entered in the detector 172 to which a bias voltage is applied, interaction occurs between the entered γ rays and a semiconductor crystal 111 included in the detector 172. This interaction generates charges comprised of an electron and a positive hole.

The generated charges are outputted from the detector 172 as γ ray detection signals. The γ ray detection signals are inputted into an amplifier 116 through a coupling capacitor 115. Here, a bleeder resistor 114 prevents the charges from being continuously accumulated in the coupling capacitor 115, thereby to prevent the output voltage of the detector 172 from excessively rising too high. The amplifier 116 converts the γ ray detection signals formed of the extremely small charges into voltages, thereby to amplify the signals.

Then, the γ ray detection signals amplified by the amplifier are converted into digital signals by an analogue/digital convertor (not shown) arranged at a downstream of the equipment 11. The digital signals thus converted are counted per energy of the γ ray by a data processor (not shown).

(On Polarization)

In the meantime, if the bias voltage such as +500V is continuously applied by the first DC power source 101 to the detector 172 in which the semiconductor crystal 111 is made of thallium bromide, polarization (or charge deviation in the semiconductor crystal) is generated in the semiconductor crystal 111. This makes the radiation detection equipment 11 cause deterioration in the energy resolution of the γ rays.

Herein, timing when the polarization occurs varies corresponding to kinds of materials used for the first electrode 112 and the second electrode 113 which are members of the detector 172, and quality of the semiconductor crystal 111. For example, the timing may be set in the range from 10 min to 50 hr.

Note the first electrode 112 and the second electrode 113 of the detector 172 function as a cathode or an anode. However, it depends on the direction of the positive and negative bias voltages whether the electrode functions as a cathode or an anode. Therefore, in order to prevent the polarization from occurring, preferably both electrodes of the detector 172 may alternatively function as a cathode and an anode each other in a well balanced manner, as described hereinafter.

(Method for Preventing Polarization)

It is needed to periodically reverse the polarity applied to the detector 172 in a short time, so that the polarization is prevented from occurring. That is, it is needed to reverse the polarity of the bias voltage, for example, from +500V to −500V and −500V to +500V. Further, it is needed to set the reversed interval shorter than 10 min.

Here, if the reversed interval is set in 10 min or more, this may deteriorate the energy resolution, causing a drawback that the energy resolution is not to be sufficiently recovered, even though the bias voltage is reversed.

Further, when the polarity of the bias voltage is to be reversed, the absolute value of the bias voltage becomes smaller for collecting the charges. This causes a break time in which the charges generated by the γ rays cannot be sufficiently extracted as signals. In other words, this causes a break time in which radiation detection cannot be performed.

If the radiation detection equipment is applied to a nuclear medicine diagnosis device and a homeland security system, preferably the detection break time may be limited as shorter as possible. Hereby, the interval needed for reversing the polarity may be set as shorter as possible.

On the other hand, the following current flows through the amplifier 116, the current corresponding to the mathematical product of the temporal change in the voltage of the smoothing capacitor 110 and the capacitance of the coupling capacitor 115. Accordingly, if the temporal change in the voltage of the smoothing capacitor 110 is large, this makes a larger current than the limiting current value flow through the amplifier 116. This flow of the larger current may damage the amplifier 116. For avoiding the damage, when the polarity of the bias voltage is reversed, the absolute value of the change rate in the bias voltage needs to be limited so that the absolute value is not exceeded from a predetermined value.

Control Method for Preventing Polarization

First Example

Hereinafter, a control method for preventing polarization of the radiation detection equipment 11 in the present embodiment will be explained as a first example, referring to FIGS. 1 and 2.

Figure 2:
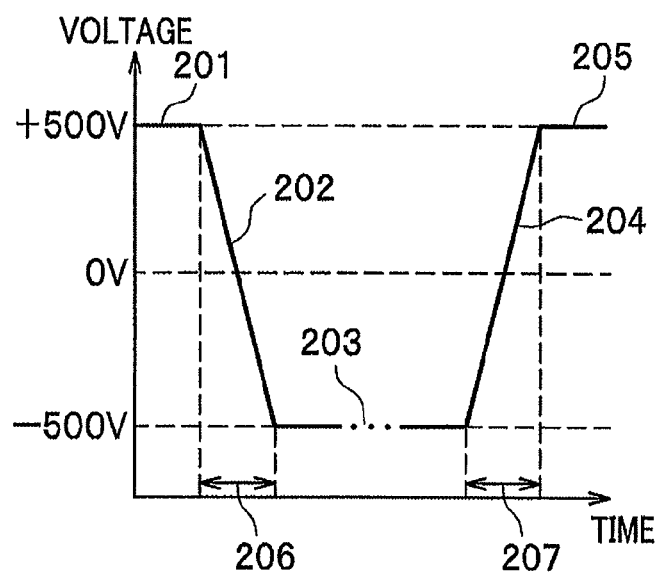
FIG. 2 is a time chart showing changes in a bias voltage applied to a semiconductor radiation detector used for the radiation detection equipment in the first embodiment of the present invention.

Herein, FIG. 2 is a time chart showing a temporal change in the bias voltage applied to the semiconductor radiation detector 172. The horizontal axis represents a time, and the vertical axis represents a voltage.

First, a control method in which a bias voltage of +500V is applied to the detector 172 will be explained. A positive DC bias voltage is supplied by the first DC power source 101 which outputs a DC voltage of 500V from a positive electrode of the power source 101. If a voltage of +500V is directly applied to the detector 172 by the first DC power source 101, this voltage application causes noise generation. Hereby, the voltage is applied to the detector 172 by the smoothing capacitor 110. That is, the bias voltage applied to the detector 172 is substantially applied by the smoothing capacitor 110.

The control unit for switches 107 closes the photoMOS relay 105 (or photoMOS relay 105: ON) and simultaneously opens the photoMOS relay 106 (or photoMOS relay 106: OFF), when a positive bias voltage is applied to the detector 172.

The smoothing capacitor 110 is charged via the constant regulative diode 108 (and constant regulative diode 109), whereby the voltage of the smoothing capacitor 110 becomes +500V. Associated with this, the bias voltage applied to the detector 172 becomes +500V. In contrast, when a bias voltage of −500V is applied to the detector 172, a negative DC voltage is supplied by the second DC power source 102 which outputs a DC voltage of 500V from a negative electrode.

The control unit for switches 107 opens the photoMOS relay 105 and simultaneously closes the photoMOS relay 106, when a negative bias voltage is applied to the detector 172. The smoothing capacitor 110 is charged via the constant regulative diode 109, whereby the voltage of the smoothing capacitor 110 becomes −500V. In the present embodiment, positive charges or negative charges are accumulated in either of the electrodes of the smoothing capacitor 110. This accumulation of the charges allows the polarity of the bias voltage applied to the detector 172 to be reversed.

The control unit for polarity integration 117 transmits command signals such as "Apply positive bias", "Apply negative bias", "Reverse bias from positive to negative", and "Reverse bias from negative to positive" to the control unit for switches 107 and the amplifier 116, based on the timing data of reversing polarity set in advance. Then, the control unit for switches 107 opens/closes the photoMOS relays 105 and 106 based on the command signals.

Characteristics of First Embodiment

In the present embodiment, the following case will be explained, in which a capacitance value of the smoothing capacitor 110 is set in 0.1 μF; each limiting current value of the constant regulative diodes 108 and 109 is set in 0.5 mA; a capacitance value of the coupling capacitor 115 is set in 1000 pF; a limiting current value of the amplifier 116 is set in 10 μA; and a period of reversing the bias voltage is set in 5 min.

First, while the command signal of "Apply positive bias" is transmitted from the control unit for polarity integration 117, the control unit for switches 107 closes the photoMOS relay 105 and simultaneously opens the photoMOS relay 106. Accordingly, positive charges are accumulated through the constant regulative diode 108 into the smoothing capacitor 110, whereby the bias voltage applied to the detector 172 becomes +500V (see the reference numeral 201 in FIG. 2).

Here, the state as indicated by the reference numeral 201 continues for 4 min and 59.7 sec (or 5 min-0.3 sec) after the bias voltage has been firstly applied to the detector 172.

Next, the control unit for polarity integration 117 has transmitted a command signal of "Reverse bias from positive to negative", and then the control unit for switches 107 closes the photoMOS relay 106 just after the control unit for switches 107 opens the photoMOS relay 105. Accordingly, the positive charges accumulated in the smoothing capacitor 110 flow through the constant regulative diode 109 into the second DC power source 102, whereby conversely the negative charges are accumulated in the smoothing capacitor 110. Then, after 0.3 sec has passed (see the state indicated by the reference numeral 206 in FIG. 2), the voltage of the smoothing capacitor 110 becomes −500V (see the state indicated by the reference numeral 203 in FIG. 2).

When the polarity of the voltage of the smoothing capacitor 110 is reversed, the temporal change in the bias voltage applied to the detector 172 is represented as a linear slope, whereby the bias voltage becomes −500V in a short period. The constant regulative diode 109 exerts the above mentioned effect.

Here, in FIG. 2 the interval shown by the reference numeral 201 is about 5 min (=5 min-0.3 sec), while the interval shown by the reference numeral 206 is 0.3 sec. Note the length of the interval shown in FIG. 2 is not correctly represented as corresponding to the actual time length. The graph of FIG. 2 is drawn so as to emphasize the interval indicated by the reference numeral 206 so that the graph clearly shows the state that the polarity of the voltage is reversed within 0.3 sec as indicated by the reference numeral 206.

Then, while the control unit for polarity integration 117 transmits the command signal of "Apply negative bias", the control for switches 107 opens the photoMOS relay 105 and simultaneously closes the photoMOS relay 106. Accordingly, negative charges are accumulated in the smoothing capacitor 110 via the constant regulative diode 109 (and constant regulative diode 108), whereby the bias voltage applied to the detector becomes −500V (see the state as indicated by the reference numeral 203).

Next, after 4 min and 59.7 sec have passed since the control unit for polarity integration 117 started transmitting the command signal of "Apply negative bias", in other words, after 5 min have passed since the command signal of "Reverse bias from positive to negative" was transmitted, on the contrary the command signal of "Reverse bias from negative to positive" is transmitted.

Then, the photoMOS relay 105 is to be closed just after the control for switches 107 has opened the photoMOS relay 106. Accordingly, negative charges accumulated in the smoothing capacitor 110 flow through the constant regulative diode 108 into the first DC power source 101. On the contrary, positive charges are to be accumulated in the smoothing capacitor 110, whereby the voltage of the smoothing capacitor 110 becomes +500V after 0.3 sec.

Note when the polarity of the voltage of the smoothing capacitor 110 is reversed, the temporal change in the bias voltage applied to the detector 172 (see the state indicated by the reference numeral 204 in FIG. 2) is represented as a linear slope, whereby the bias voltage becomes +500V in a short period. The constant regulative diode 108 exerts the above mentioned effect.

After that, the control unit for polarity integration 117 again transmits the command signal of "Apply positive bias", whereby the bias voltage applied to the detector 172 is kept at +500V (see the state indicated by the reference numeral 205).

Accordingly, the pieces of the detection break time 206 and 207 (indicated by the reference numerals 206 and 203) are respectively to be 0.3 sec. Therefore, during the radiation detection for 10 min, totally the break time of 0.6 sec is caused. However, this interval is sufficiently short time if the radiation detection equipment is applied to a nuclear medicine diagnosis device and a homeland security system, resulting in no problem.

Herein, at the same time, it is needed to prevent the amplifier 116 from being damaged by controlling the current such that a larger current than the limiting current value does not flow through the amplifier 116.

In the present embodiment, the capacitance value of the coupling capacitor 115 is set in 1000 pF, and the limiting current value of the amplifier 116 is set in 10 µA. Hereby, it is needed to control the current so that the maximum absolute value of the voltage change rate of the smoothing capacitor 110 does not exceed over 10000V/sec.

In the example shown in FIG. 2, the maximum absolute value of the voltage change rate is about 3300V/sec (=500×2/0.3). Since the capacitance value of the coupling capacitor 115 is 1000 pF, it is calculated that the maximum current of 3.3 µA (=1000×10-12×3300) flows through the amplifier 116. The calculated value is lower than the limiting current value (10 µA) of the amplifier 116. Thus, there is no probability that the amplifier 116 is to be damaged.

Here, it is preferable that pieces of the detection break time 206 and 207 (indicated by the reference numerals 206 and 207 in FIG. 2) are as shorter as possible from the viewpoint of full detection. However, the shorter the detection break time is, the larger the voltage change rate becomes when the polarity is reversed. This causes the current flowing into the amplifier 116 to become larger, which may cause an unfavorable accident in the light of the reliability on the devices and components including the amplifier of FIG. 1, as well as the cost performance of the radiation detection equipment 11.

If the radiation detection equipment 11 is applied to a system in a field where a shorter detection break time is demanded, the pieces of the detection break time 206 and 207 of FIG. 2 (indicated by the reference numerals 206 and 207 in FIG. 2) may be appropriately determined by taking the above mentioned viewpoints in consideration.

The γ ray detection signal inputted to the amplifier 116 is converted to a positive charge or a negative charge corresponding to the polarity of the bias voltage applied to the detector 172. Herein, it is needed to reverse the polarity of the amplifier 116 associated with the polarity of the charge. Therefore, the command signals of "Apply positive bias", "Apply negative bias", "Reverse bias from positive to negative" and "Reverse bias from negative to positive" which are transmitted from the control unit for polarity integration 117 into the amplifier 116 are respectively converted to the polarities of the amplifier 116 as "Correspond to negative charge", "Correspond to positive charge", "Reverse negative charge corresponding to, positive charge corresponding", and "Reverse positive charge corresponding to negative charge corresponding".

FIGS. 3A-3D are schematic diagrams each showing a γ ray energy spectrum by a $^{57}$Co radiation source, the spectrum being detected by the radiation detection equipment 11 in the present embodiment. That is, FIGS. 3A, 3B, 3C and 3D respectively indicate the spectra in the states: just after the bias voltage has been applied (FIG. 3A); after 5 min (FIG. 3B); after 535 min (FIG. 3C); and after 540 min (FIG. 3D).

In FIGS. 3A, 3B, 3C and 3D, the horizontal axis represents the channel number of the energy channel. Here, a variety of γ rays with different energies are assigned to the respective channels (or energy channels), corresponding to the difference in energies (that is, per predetermined range of energy).

For example, in FIG. 3A, the γ ray energy of substantial 122 keV is assigned to the energy channel near the substantial No. 430 channel. As the γ ray energy increases, energy channels with the larger numbers are assigned in that order.

Further, in FIGS. 3A, 3B, 3C and 3D, the vertical axis represents the detection rate of the γ ray at each energy channel (that is, counts per min: the count number per one minute). Here, the γ ray energies are continuously distributed, while it is practical to count the γ rays in the predetermined energy range (or width) for the detection. Accordingly, in a general detection method, the γ rays are separately detected per energy channel corresponding to the predetermined energy range.

Note FIGS. 3A, 3B, 3C and 3D respectively show the spectrum that the γ rays separately detected per energy channel are continuously represented, in which the horizontal axis indicates the energy channel.

In FIG. 3A, a peak is observed for the detection rate of the energy channel corresponding to the energy of substantial 122 keV. The energy resolution at such a peak is represented by the following equation, when a half-width of the peak is defined as a range (or width) of the channel number of the detection rate, in which the range is determined as the width of the peak at the half level of the maximum height thereof.

Energy Resolution=(Number of Channels in Half-width)/(Number of Channels in Peak Bottom)

Herein, when the energy resolution is represented as a percentage (%), such a value is calculated by multiplying the original value obtained in the equation by 100.

Further, the energy resolution represents a standard of the distinguishable energies. Hereby, this means that the smaller value the energy resolution has, the higher the detection performance is.

Note in the 4 diagrams of FIGS. 3A, 3B, 3C and 3D, each energy resolution at 122 keV is in substantial 8%. At least over the period of 540 min (or 9 hr), the energy resolution is kept in substantial 8% and no polarization occurs, allowing the stable radiation detection to be realized.

As mentioned hereinafter, nuclear medicine diagnosis devices such as SPECT imaging equipment 600 (see FIG. 7) and PET imaging equipment 700 (see FIG. 8) are not generally utilized in a continuous manner, for 540 min or the more (9 hr) per day. Therefore, if the characteristics of the energy resolution for 540 min (9 hr) are not changed, substantially the initial characteristics are expected to be secured for a long term.

As mentioned above, the radiation detection equipment 11 in the present invention enables the polarization to be prevented thereby to realize the stable radiation detection, without inserting thallium layers between the cathode and the thallium bromide crystal, and between the anode and the thallium bromide crystal, in the thallium bromide based radiation detector.

Characteristics in Comparative Example with Elongated Polarity Reversing Period of Bias Voltage In the first embodiment of the radiation detection equipment, the period of reversing the polarity of the bias voltage applied to the detector 172 is set in shorter than 10 min, more specifically set in 5 min. In contrast, a Comparative Example will be explained, in which the period of reversing the polarity of the bias voltage is set in 10 min or more. Here, by comparing the results of the first embodiment and the Comparative Example, the outstanding features and advantages of the present invention will be presented, in which the period of reversing the polarity of the bias voltage is set in shorter than 10 min.

In the first embodiment of the present invention, the period of reversing the polarity of the bias voltage applied to the detector. 172 in the radiation detection equipment 11 is set in 5 min. On the contrary, the period of reversing the polarity of the bias voltage is set in 20 min. The other construction in the Comparative Example is the same as that in the first embodiment.

Figure 5A:
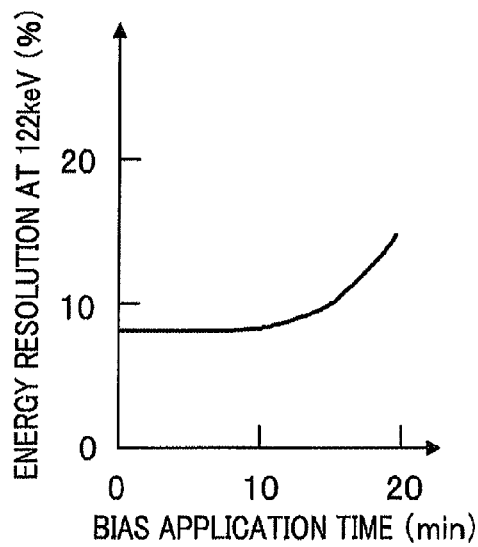
FIGS. 5A to 5D are response characteristics diagrams each showing a relationship between a bias application time and energy resolution at 122 keV in radiation detection equipment of a comparative example.
Figure 5B:
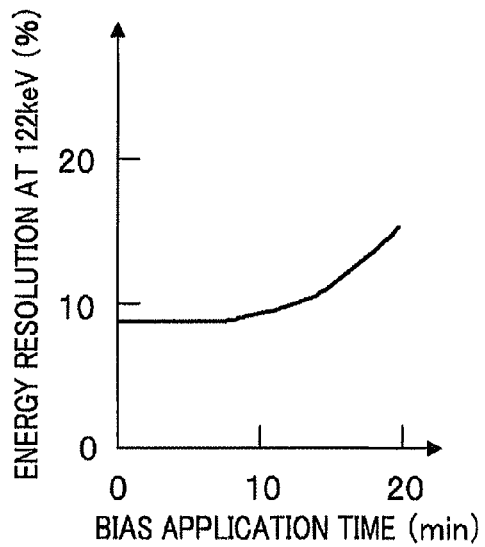
Figure 5C:
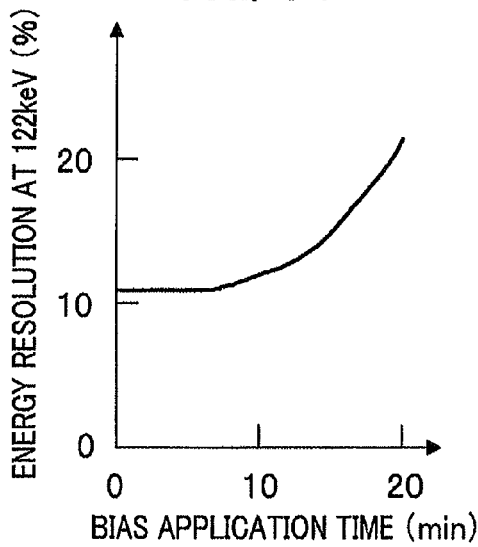
Figure 5D:
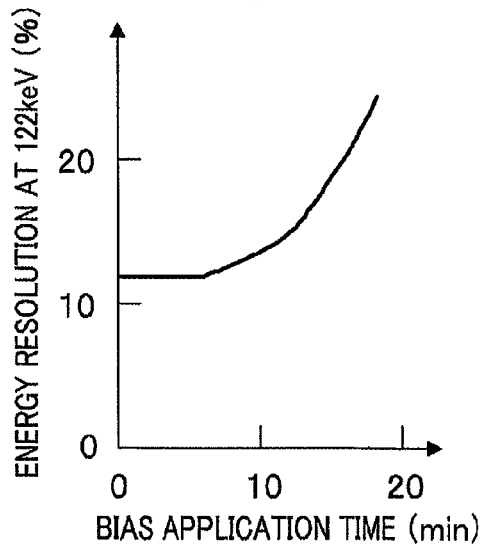

FIGS. 5A-5D are graphic diagrams each showing a relationship between a bias application time and energy resolution at 122 keV. That is, FIGS. 5A, 5B, 5C and 5D respectively represent the results when a positive bias voltage is initially applied (FIG. 5A); when the polarity is reversed and then a negative bias voltage is applied (FIG. 5B); when the polarity is reversed again and then the second positive bias voltage is applied (FIG. 5C); and when the polarity is reversed again and then the second negative bias voltage is applied (FIG. 5D).

In FIGS. 5A-5D, the horizontal axis represents the bias application time (min), and the vertical axis represents the energy resolution (%) at 122 keV.

Figure 6A:
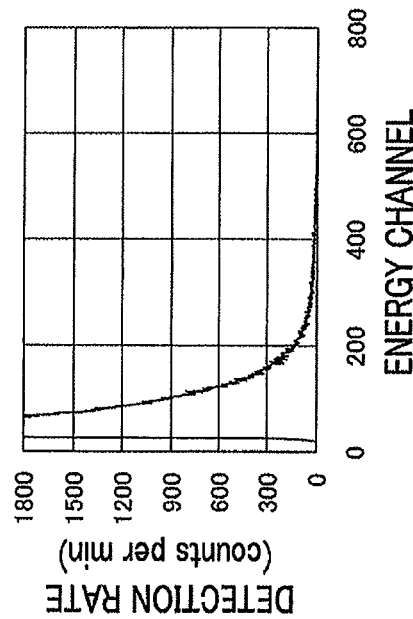
FIGS. 6A and 6B are schematic diagrams each showing a γ-ray energy spectrum of a $^{57}$Co radiation source detected by radiation detection equipment of a comparative example.
Figure 6B:
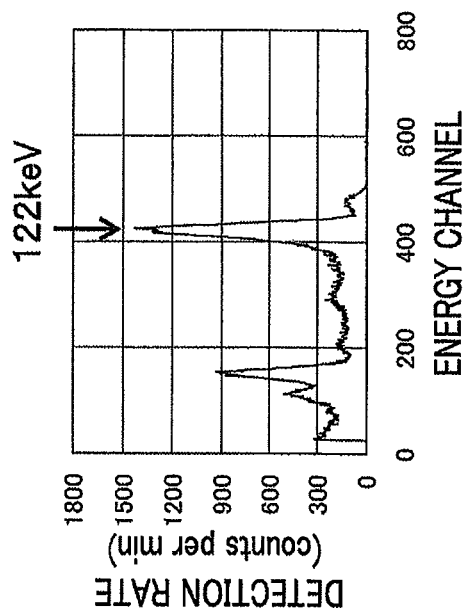

FIGS. 6A and 6B are schematic diagram each showing a γ-ray energy spectrum of a $^{57}$Co radiation source detected by radiation detection equipment of a comparative example. FIGS. 6A and 6B respectively show the energy spectrum properties just after a bias voltage has been applied (FIG. 6A), and in 78 minutes totally after the first application of the bias voltage has been started (FIG. 6B).

In FIGS. 6A and 6B, the horizontal axis represents the energy channel, and the vertical axis represents the detection rate of the γ ray (counts per min).

As shown in FIGS. 5A and 6A, each energy resolution at 122 keV is in substantial 8%, when the positive bias voltage is initially applied.

Then, as shown in FIG. 5A, the energy resolution is kept in substantial 8% in the period of 10 min since the positive bias voltage has been initially applied. However, in a period after 10 min has passed, the energy resolution becomes generally deteriorated. This deterioration of the energy resolution is indicated as the phenomenon that the characteristic curve goes up after 10 min have passed, in FIG. 5A.

In the period of 20 min of the bias application time (min) of FIG. 5A, the energy resolution greatly comes to be deteriorated. However, at this timing, namely after 20 min has passed, if the polarity of the bias voltage is reversed, so as to apply a negative bias voltage, the energy resolution becomes partially improved, reaching substantial 90. That is, the energy resolution is recovered to be in substantial 9%, while the energy resolution is not recovered up to substantial 8% which is an initial rate. Note the recovery process is not shown in FIGS. 5A-5D.

Herein, the state that the energy resolution is recovered up to substantial 9% corresponds to the state at 0 min of the bias application time in FIG. 5B.

As shown in FIG. 5B, if a negative bias voltage is continuously applied since the energy resolution has been recovered in substantial 9%, the energy resolution is kept in substantial 9% at least for 8 min. However, after that, the energy resolution comes to be deteriorated, and the deterioration becomes marked after about 10 min have passed. The deterioration of the energy resolution is indicated in FIG. 5B, by the phenomenon that the characteristic curve goes up after the bias application time of 10 min.

Next, at the bias application time of 20 min in FIG. 5B, the energy resolution becomes markedly deteriorated. However, if at that time, namely after 20 min have passed, if the polarity of the bias voltage is reversed thereby to apply a positive bias voltage, the energy resolution is partially recovered up to substantial 11%. As mentioned above, the energy resolution comes to be recovered up to substantial 11%, while the energy resolution is not recovered up to substantial 8% as the initial value. Further, the energy resolution is not to be recovered even in substantial 9% which is the value at 0 min in the bias application time shown in FIG. 5B.

Herein, the state that the energy resolution is recovered up to substantial 11% corresponds to the state at 0 min of the bias application time in FIG. 5C.

As shown in FIG. 5C, if a positive bias voltage is continuously applied again since the energy resolution has been recovered in substantial 11%, the energy resolution is kept in substantial 11% at least for 6 min. However, after that, the energy resolution comes to be deteriorated, and the deterioration becomes marked as the time passes. The deterioration of the energy resolution is indicated in FIG. 5C, by the phenomenon that the characteristic curve goes up after the bias application time of substantial 10 min has passed.

Next, at the bias application time of 20 min in FIG. 5C, the energy resolution becomes markedly deteriorated. However, if at that time, namely after 20 min have passed, if the polarity of the bias voltage is reversed thereby to apply a negative bias voltage, the energy resolution is partially recovered up to substantial 12%.

Herein, the state that the energy resolution is recovered up to substantial 12% corresponds to the state at 0 min of the bias application time in FIG. 5D.

As shown in FIG. 5D, if a negative bias voltage is continuously applied again since the energy resolution has been recovered in substantial 12%, the energy resolution is kept in substantial 12% at least for 5 min. However, after that, the energy resolution comes to be deteriorated, and the deterioration becomes marked as the time passes.

Then, after 18 min have passed, as shown in FIG. 6B, the peak at substantial 122 keV disappears from the energy spectrum.

As mentioned above, if the period of the bias application time is 20 min, the energy resolution deteriorates in the period of the bias application time for reversing the polarity. Further, even though the polarity of the bias voltage is reversed, the energy resolution is not to be recovered, whereby the deterioration of the energy resolution is continuously accumulated.

As described hereinbefore, the radiation detection equipment of the Comparative Example cannot maintain the good energy resolution, which prevents the stable radiation detection from being performed.

In contrast, the radiation detection equipment 11 in the first embodiment of the present invention can maintain the energy resolution in substantial 8% at least over 540 min (9 hr) and perform the stable radiation detection without causing any polarization.

This advantageous effect is exerted by the feature of the present embodiment that the period of reversing the bias voltage applied to the detector 172 is set in shorter than 10 min in the radiation detection equipment 11 of the first embodiment of the present invention, while the period of reversing the bias voltage applied to the detector is set in 10 min or more in the radiation detection equipment of the Comparative Example.

Second Embodiment of Radiation Detection Equipment

Figure 4:
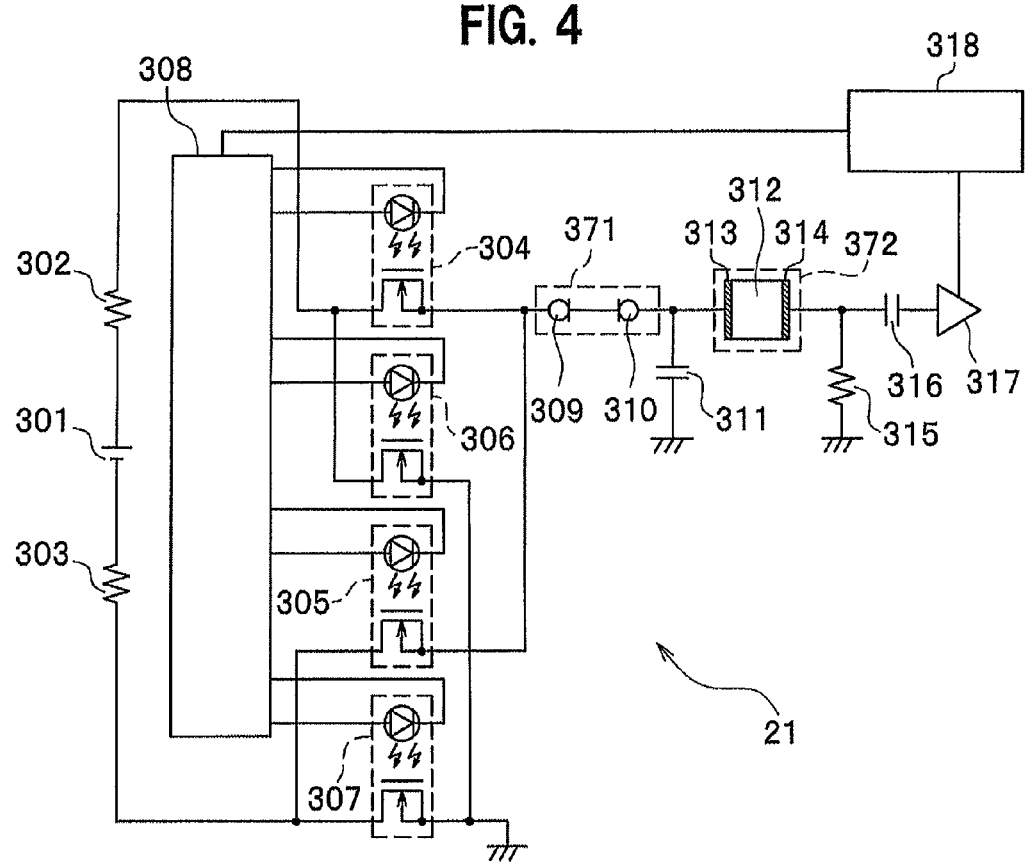
FIG. 4 is a block diagram of a circuit structure of the radiation detection equipment in a second embodiment of the present invention.

FIG. 4 is a bloc diagram showing a circuit structure of the radiation detection equipment in a second embodiment of the present invention. As shown in FIG. 4, radiation detection equipment 21 comprises: a semiconductor radiation detector (hereinafter, simply called a detector) 372 including a semiconductor crystal 312 made of thallium bromide, a first electrode 313 made of gold and a second electrode 314 also made of gold, respectively arranged at opposite surface sides of the semiconductor crystal 312; a smoothing capacitor 311 of applying a voltage to the detector 372; and a DC power source 301 of accumulating positive charges or negative charges in either of electrodes of the smoothing capacitor 311.

The radiation detection equipment 21 further comprises: a first constant regulative diode 309 which is connected by integrating the polarity of the constant-current characteristics so that a current flows from the DC power source 301 to either of the electrodes of the smoothing capacitor 311; and a second constant regulative diode 310 which is connected by integrating the polarity of the constant-current characteristics so that a current flows from either of the electrodes of the smoothing capacitor 311 to the DC power source 301.

Further, the radiation detection equipment 21 comprises: a first photoMOS relay 304 connected with a wire which connects the DC power source 301 and either of the electrodes of the smoothing capacitor 311; a second photoMOS relay 305 connected with a wire which connects a negative electrode of the DC power source 301 and either of the electrodes of the smoothing capacitor 311; a third photoMOS relay 306 connected with a ground wire at the positive electrode side of the DC power source 301; and a fourth photoMOS relay 307 connected with a ground wire at the negative electrode side of the DC power source 301.

Note the first constant regulative diode 309 and the second constant regulative diode 310 are connected in series so that the respective polarities are reversed each other, thereby to construct the current regulator 371.

Further, a protection resistor 302 is arranged between the positive electrode of the DC power source 301 and the first photoMOS relay 304, a protection resistor 303 is arranged between the negative electrode of the DC power source 301 and the second photoMOS relay 305, the fourth photoMOS relay 307. Those protection resistors 302 and 303 are provided as resistors for preventing excess currents.

Herein, a control unit for switches 308 controls opening/closing of the photoMOS relays 304-307.

Further, a bleeder resistor 315 and one of electrodes of a coupling capacitor 316 are connected with the detector 372. An amplifier 317 which amplifies a signal of the detector 372 is connected with the other electrode of the coupling capacitor 316.

Moreover, a control unit for polarity integration 318 which controls opening/closing of the photoMOS relays 304-307, and timing of reversing a polarity of the amplifier 317 is connected with the control unit for switches 308 and the amplifier 317.

Herein, the other electrode of the smoothing capacitor 311, and one of the electrodes of the bleeder resistor 315 are respectively connected with ground wires.

If radiations such as γ rays are to be detected by the radiation detection equipment 21, a positive or negative bias voltage for collecting charges (for example, +500V or −500V) is applied between a first electrode 313 and a second electrode 314 of the detector 372 by the DC power source 301 and the smoothing capacitor 311.

Here, the steps of processing γ ray detection signals when the γ rays are entered into the detector 372 are the same as in the first embodiment.

In the meantime, similarly to the first embodiment, polarization occurs when a bias voltage such as +500V is continuously applied to the detector 372 of which semiconductor crystal 312 is made of thallium bromide.

Hereinafter, a control method for preventing polarization of the radiation detection equipment 21 in the present embodiment will be explained as a second example, referring to FIGS. 4 and 2.

Control Method for Preventing Polarization

Second Example

First, a control method in which a bias voltage of +500V is applied to the detector 372 will be explained. If a voltage of +500V is directly applied to the detector 372 by the DC power source 301, this causes noise generation. Hereby, the voltage is applied to the detector 372 by the smoothing capacitor 311.

The control unit for switches 308 closes the photoMOS relays 305 and 307 and simultaneously opens the photoMOS relays 305 and 306, when a positive bias voltage is applied to the detector 372.

The smoothing capacitor 311 is charged via the constant regulative diode 309 (and constant regulative diode 310), whereby the voltage of the smoothing capacitor 311 becomes +500V. Associated with this, the bias voltage applied to the detector 372 becomes +500V.

In contrast, when a bias voltage of −500V is applied to the detector 372, the control unit for switches 308 opens the photoMOS relays 304 and 307, and simultaneously closes the photoMOS relays 305 and 306, when a bias voltage of −500V is applied to the detector 372. The smoothing capacitor 311 is charged via the constant regulative diode 310, whereby the voltage of the smoothing capacitor 311 becomes −500V.

The control unit for polarity integration 318 transmits command signals such as "Apply positive bias", "Apply negative bias", "Reverse bias from positive to negative", and "Reverse bias from negative to positive" to the control unit for switches 308 and the amplifier 317, based on the timing data of reversing polarity set in advance. Then, the control unit for switches 308 opens/closes the photoMOS relays 304-307 based on the command signals.

Characteristics of Second Embodiment

In the present embodiment, the following case will be explained, in which a capacitance value of the smoothing capacitor 311 is set in 0.1 μF; each limiting current value of the constant regulative diodes 309 and 310 is set in 0.5 mA; a capacitance value of the coupling capacitor 316 is set in 1000 pF; a limiting current value of the amplifier 317 is set in 10 μA; and a period of reversing the bias voltage is set in 5 min.

First, while the command signal of "Apply positive bias" is transmitted from the control unit for polarity integration 318, the control unit for switches 308 closes the photoMOS relays 304 and 307, and simultaneously opens the photoMOS relays 305 and 306. Accordingly, positive charges are accumulated through the constant regulative diode 309 into the smoothing capacitor 311, whereby the bias voltage applied to the detector 372 becomes +500V (see the reference numeral 201 in FIG. 2).

Here, the state as indicated by the reference numeral 201 continues for 4 min and 59.7 sec after the bias voltage has been firstly applied to the detector 372.

Next, the control unit for polarity integration 318 has transmitted a command signal of "Reverse bias from positive to negative", and then the control unit for switches 308 closes the photoMOS relays 305 and 306 just after the control unit for switches 308 opens the photoMOS relays 304 and 307. Accordingly, the positive charges accumulated in the smoothing capacitor 311 flow through the constant regulative diode 310 into the DC power source 301, whereby on the contrary the negative charges are accumulated in the smoothing capacitor 311. Then, after 0.3 sec has passed, the voltage of the smoothing capacitor 311 becomes −500V.

When the polarity of the voltage of the smoothing capacitor 311 is reversed, the temporal change in the bias voltage applied to the detector 372 is represented as a linear slope (see the state as indicated by the reference numeral 202 in FIG. 2), whereby the bias voltage becomes −500V in a short period. The constant regulative diode 310 exerts the above mentioned effect.

Then, while the control unit for polarity integration 318 transmits the command signal of "Apply negative bias", the control for switches 308 opens the photoMOS relays 304 and 307, and simultaneously closes the photoMOS relays 305 and 306. Accordingly, negative charges are accumulated in the smoothing capacitor 311 via the constant regulative diode 310, whereby the bias voltage applied to the detector 372 becomes −500V (see the state as indicated by the reference numeral 203).

Next, after 4 min and 59.7 sec have passed since the control unit for polarity integration 318 started transmitting the command signal of "Apply negative bias", in other words, after 5 min have passed since the command signal of "Reverse bias from positive to negative" was transmitted, on the contrary the command signal of "Reverse bias from negative to positive" is transmitted. Then, the control for switches 308 closes the photoMOS relays 304 and 307, just after the control for switches 308 has opened the photoMOS relays 305 and 306.

Accordingly, negative charges accumulated in the smoothing capacitor 311 flow through the constant regulative diode 309 into the DC power source 301. On the contrary, positive charges are to be accumulated in the smoothing capacitor 311, whereby the voltage of the smoothing capacitor 110 becomes +500V after 0.3 sec.

After that, the control unit for polarity integration 318 again transmits the command signal of "Apply positive bias", whereby the bias voltage applied to the detector 372 is kept at +500V (see the state indicated by the reference numeral 205).

Accordingly, the pieces of the detection break time 206 and 207 are respectively to be 0.3 sec, similarly to the first embodiment. Therefore, during the radiation detection for 10 min, totally the break time of 0.6 sec is caused. However, this interval is sufficiently short time if the radiation detection equipment is applied to a nuclear medicine diagnosis device and a homeland security system, resulting in no problem.

Herein, the maximum absolute value of the voltage change rate in the smoothing capacitor 311 is about 3300V/sec. Since it is calculated that the maximum current of 3.3 μA flows through the amplifier 317, the calculated value is lower than the limiting current value of the amplifier 317.

The γ ray detection signal inputted to the amplifier 317 is converted to a positive charge or a negative charge corresponding to the polarity of the bias voltage applied to the detector 372. Herein, it is needed to reverse the polarity of the amplifier 317 associated with the polarity of the charge. Therefore, the command signals of "Apply positive bias", "Apply negative bias", "Reverse bias from positive to negative" and "Reverse bias from negative to positive" which are transmitted from the control unit for polarity integration 318 into the amplifier 317 are respectively converted to the polarities of the amplifier 317 as "Correspond to negative charge", "Correspond to positive charge", "Reverse negative charge corresponding to positive charge corresponding", and "Reverse positive charge corresponding to negative charge corresponding".

Here, the energy resolution at substantial 122 keV of γ rays from a $^{57}$Co radiation source is kept in substantial 8%, which is detected by the radiation detection equipment 21 in the present embodiment. That is, at least over the period of 540 min (or 9 hr), the energy resolution is kept in substantial 8% just after the bias voltage has been applied, and no polarization occurs. This allows the stable radiation detection to be realized, similarly to the case that the radiation detection equipment 11 is used in the first embodiment.

As mentioned hereinbefore, the radiation detection equipment 21 in the present embodiment enables the number of the DC power sources to be reduced, while the number of the photoMOS relays is increased, compared to the radiation detection equipment 11 in the first embodiment. Generally, the cost needed for a DC power source is higher than the cost needed for a photoMOS relay. Hereby, this allows the production cost of the radiation detection equipment 21 in the present embodiment to be more reduced than that of the radiation detection equipment 11 in the first embodiment.

First Example of Applying Radiation Detection Equipment of Present Embodiment to Nuclear Medicine Diagnosis Device The radiation detection equipment 11 in the first embodiment and the radiation detection equipment 21 in the second embodiment as explained hereinbefore can be applied to a nuclear medicine diagnosis device.

Figure 7:
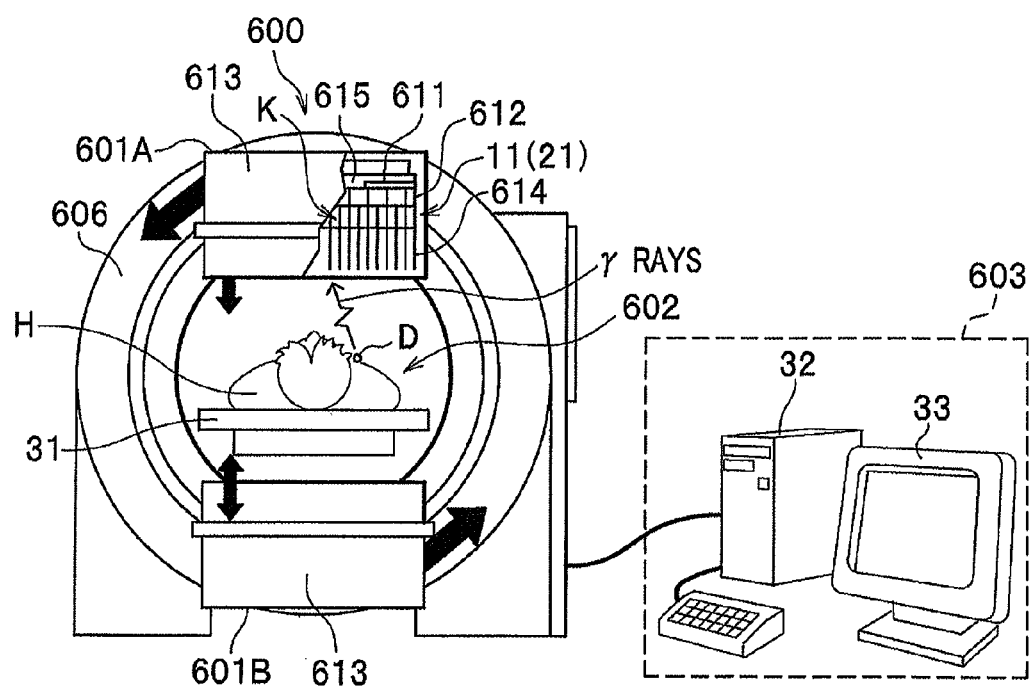
FIG. 7 is a schematic construction diagram of equipment for single photon emission computed tomography (or SPECT equipment) shown as a first application example in which the radiation detection equipment of the present invention is used for the nuclear medicine diagnosis device.

Here, FIG. 7 is a construction diagram showing a case in which the radiation detection equipment 11 in the first embodiment or the radiation detection equipment 21 in the second embodiment is applied to the SPECT imaging equipment 600 which is used for a nuclear medicine diagnosis device.

In FIG. 7, the SPECT imaging equipment 600 comprises: a pair of radiation detection blocks 601A and 601B respectively arranged at an upper position and at a lower position, a rotatable support 606, a bed 31 and an image data composing device 603. Herein, the above described components are arranged so that a cylindrical detection space 602 is surrounded at the central part of the equipment 600.

Here, the radiation detection block 601A arranged at an upper position has a plurality of radiation detection units 611, unit support members 615 and shade/electromagnetic shields 613. The radiation detection unit 611 includes multiple pieces of the radiation detection equipment 11 (or 21), circuit boards 612 and collimators 614. The radiation detection block 601B arranged at a lower position has the same structure as the block 601A. Further, the image data composing device 603 is comprised of a data processor 32 and a display 33.

The pair of radiation detection blocks 601A and 601B is arranged on the rotatable support 606 such that the respective positions are shifted by 180° in the circumferential direction of the rotatable support 606. More specifically, the respective unit support members 615 (note FIG. 7 shows only one of the members 615) of the radiation detection blocks 601A and 601B are attached to the rotatable support 606 at the separated positions shifted by 180° in the circumferential direction of the rotatable support 606. Further, a plurality of the radiation detection units 611 each including the circuit board 612 are detachably attached to the unit support member 615.

The multiple pieces of radiation detection equipment 11 are respectively arranged in a multistage manner in the state that each piece of the equipment 11 is attached to the circuit board 612 in the space K which is partitioned by the collimators 614. Each collimator 64 is made of a radiation shielding material (such as lead, tungsten or the like), and formed to have a number of radiation passages through which radiations (such as γ rays) pass.

All of the circuit boards 612 and collimators 614 are arranged inside the shade/electromagnetic shield 613 mounted on the rotatable support 606. The shade/electromagnetic shield 613 shields the radiation detection equipment 11 or the like from the electromagnetic waves other than the γ rays.

When such SPECT imaging equipment 600 is operated, a bed 31 on which a subject H to whom a radioactive drug is dosed is moved, whereby the subject H is also moved to the place between a pair of radiation detection blocks 601A and 601B. Then, a rotatable support 601 is rotated, thereby to rotate the respective radiation detection blocks 601A and 601B around the subject H. Accordingly, the SPECT imaging equipment 600 starts the radiation detection.

Then, γ rays are emitted from an accumulation unit D (that is, diseased part) inside the subject H, a radioactive drug being accumulated in the accumulation unit D. The emitted γ rays enter the radiation detection equipment 11 via passing through the radiation passages in the collimator 614. Hereby, the radiation detection equipment 11 outputs γ ray signals. The γ ray signals are counted by the data processor 32 per γ ray energy, whereby the resulting data or the like are displayed on the display 33.

Note in FIG. 7, the radiation detection blocks 601A and 601B are rotated as indicated by a big arrow with being supported by the rotatable support 606, so as to take images and detect radiations via changing the angle between the subject H and each block. Further, the radiation detection blocks 601A and 601B can be moved upward and downward as shown small arrows, allowing the distance between the subject H and each block to be changed.

The radiation detection equipment 11 (or 21) applied to the above mentioned SPECT imaging equipment 600 can prevent polarization, and stably detect radiations over a long time. This operation can be performed without inserting thallium layers between a cathode and a thallium bromide crystal, and between an anode and a thallium bromide crystal, in the thallium bromide based radiation detector. Accordingly, this enables lower priced radiation detection equipment to be realized because the step of disposing the thallium layers can be skipped, which prevents the cost from being increased. Further, this also enables a nuclear medicine diagnosis device using the lower priced radiation detection equipment to be provided at a lower price.

The radiation detection equipment 11 in the first embodiment and the radiation detection equipment 21 in the second embodiment as mentioned hereinbefore, can be applied to not only the above described SPECT imaging equipment 600 but also gamma camera equipment and PET imaging equipment or the like.

Next, an example will be explained, in which the radiation detection equipment of the present invention is applied to PET imaging equipment.

Figure 8:
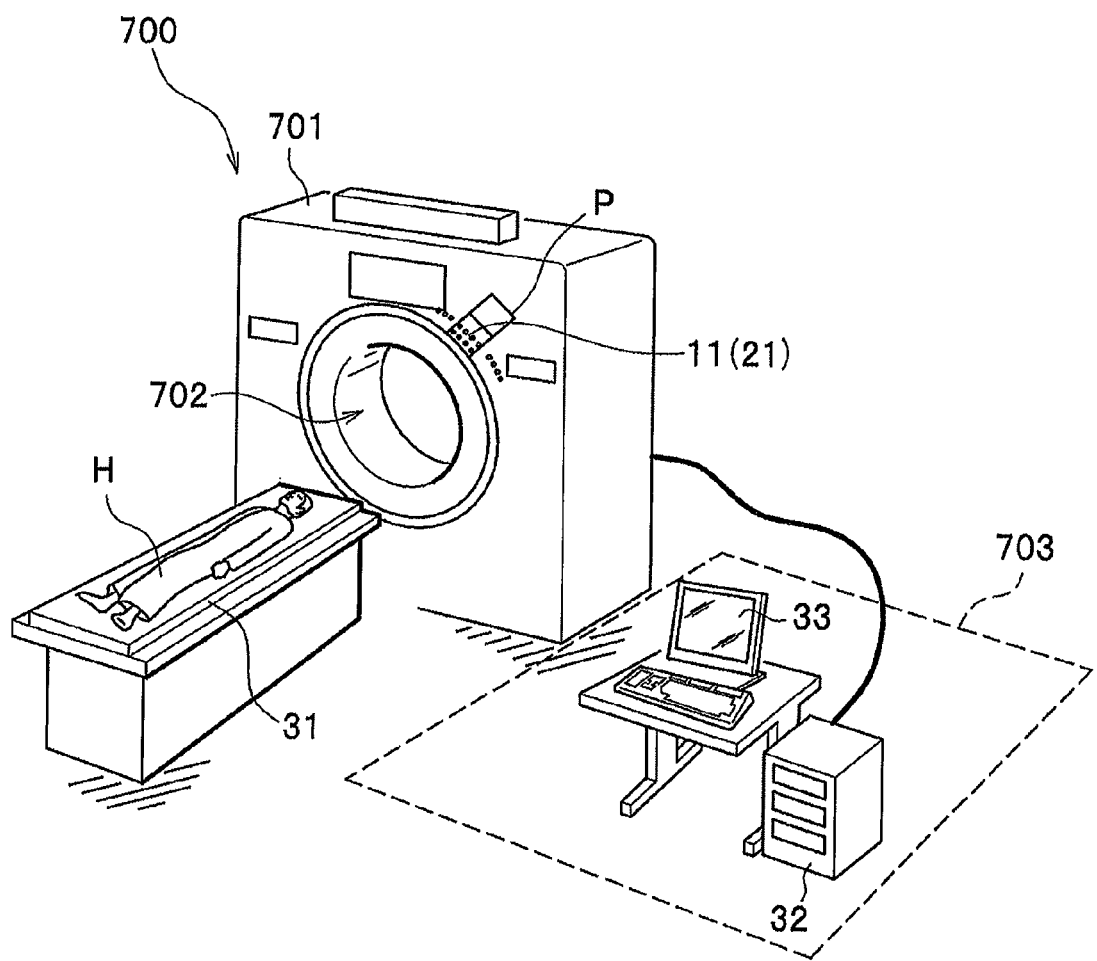
FIG. 8 is a schematic construction diagram of imaging equipment for positron emission tomography (or PET equipment) shown as a second application example in which the radiation detection equipment of the present invention is used for the nuclear medicine diagnosis device.

Second Example of Applying Radiation Detection Equipment of Present Embodiment to Nuclear Medicine Diagnosis Device FIG. 8 is a construction diagram showing a case in which the radiation detection equipment 11 in the first embodiment or the radiation detection equipment 21 in the second embodiment is applied to the PET imaging equipment 700 which is used for a nuclear medicine diagnosis device.

In FIG. 8, the PET imaging equipment 700 comprises: imaging equipment 701 having a cylindrical detection space 702 at the central part of the equipment 701; a bed 31 supporting a subject H and movable in the longitudinal direction; and an image data composing device 703. Note the image data composing device 703 is comprised of a data processor 32 and a display 33.

In the imaging equipment 701, a printed board P incorporating many pieces of radiation detection equipment 11 (or 21) on a circuit board is arranged so as to surround the detection space 702.

Such PET imaging equipment 700 includes a digital ASIC having the data processing functionality (Application Specific Integrated Circuit for digital circuit, or called digital data processing circuit; not shown in FIG. 8). The digital ASIC creates a packet including energy values of gamma rays, time and a detection channel ID (or Identification) of the radiation detection equipment 11 (or 21). Then, the packed thus created is to be inputted into the data processor 32.

At the detection, the radiation detection equipment 11 (or 21) detects the γ rays emitted as derived from the radioactive drug inside the subject H body. More specifically, when a positron emitted from the radioactive drug for PET imaging is annihilated, a pair of γ rays is emitted in opposite directions by about 180°, and separate detection channels in many pieces of the radiation detection equipment 11 (or 21) detect the pair of γ rays. The γ ray detection signal thus detected is inputted into the corresponding digital ASIC, thereby the above mentioned signal processing is performed. Then, the data on the position of the detection channel which has detected the γ ray as well as the data on the detection time of the γ ray are inputted into the data processor 32.

Then, the data processor 32 counts the pair of γ rays generated via the annihilation of the single positron as one count (that is, coincidence counting). The data processor 32 specifies the positions of the 2 detection channels, which have detected the pair of γ rays, based on the positional data of the 2 channels. Further, the data processor 32 creates tomographic image data (or image data) of the subject H at an accumulated position of the radioactive drug, in other words, at a tumor position, by using the number of the counts acquired in the coincidence counting as well as the positional data of the detection channels. The tomographic image data are displayed on the display 33.

The radiation detection equipment 11 (or 21) applied to the above mentioned PET imaging equipment 700 can prevent polarization, and stably detect radiations over a long time. This operation can be performed without inserting thallium layers between a cathode and a thallium bromide crystal, and between an anode and a thallium bromide crystal, in the thallium bromide based radiation detector. Accordingly, this enables lower priced radiation detection equipment to be realized because the step of disposing the thallium layers can be skipped, which prevents the cost from being increased. Further, this also enables a nuclear medicine diagnosis device using the lower priced radiation detection equipment to be provided at a lower price.

Other Embodiments

As mentioned hereinbefore, in the first embodiment of FIG. 1 and the second embodiment of FIG. 4, gold is applied to a material of the first electrodes (112 and 313) and a material of the second electrode (113 and 314), in the radiation detection equipment of the present invention. However, platinum or palladium may be applied to the material.

Further, in the first embodiment of FIG. 1 and the second embodiment of FIG. 4, the first constant regulative diodes (108 and 309) and the second constant regulative diodes (109 and 310) are used as connected in series. However, 3 or more constant regulative diodes may be used in a combined manner. Alternatively, other types of devices or circuits may be used if those units have constant regulative characteristics.

Moreover, in the first embodiment of FIG. 1 and the second embodiment of FIG. 4, the examples in which the photoMOS relays 105, 106, 304, 305, 306, and 307 are utilized. However, since the photoMOS relay functions as a relay, it is not necessary to use a photoMOS relay. A general relay can be used, if such a relay secures the reliability.

Furthermore, in the first embodiment of FIG. 1, referring to the time chart which indicates the change in the bias voltage of FIG. 2, the example is shown in which the polarities of the bias voltage applied to the semiconductor radiation detector 172 are periodically reversed per 5 min. However, other intervals may be selected, if such intervals are within 10 min or less.

Further, the time needed for reversing the polarity is set in 0.3 sec, while other period (for example, within 0.1 sec or 1 sec) may be set for the time. Note the time needed for reversing the polarity is set via totally taking the following factors into consideration. The factors includes the selected application field and cost performance on the radiation detection equipment and the nuclear medicine diagnosis device using the radiation detection equipment.

Further, the bias voltage applied to the semiconductor radiation detector 172 may have a value of 500V or less. That is, an appropriate voltage can be set thereto associated with a shape and structure of the semiconductor radiation detector 172.

Further, FIGS. 7 and 8 show the examples of the data processor and the display 33 as the image data composing device 603 and 703. However, since there may be a variety of forms in data processing, it is not always needed to use the exemplary combination of the data processor 32 and the display 33.

As described hereinbefore, according to the present invention, the thallium bromide based radiation detector can stably detect radiations without causing increase in the cost needed for depositing thallium layers. This allows lower priced radiation detection equipment and a lower priced nuclear medicine diagnosis device using the radiation detection equipment to be provided.

Supplement of Present Invention and Present Embodiments

As explained hereinbefore, it has been demonstrated that the insertion of the thallium layers between a general cathode and a thallium bromide crystal, and between a general anode and the thallium bromide crystal, in the semiconductor radiation detector composed of thallium bromide can prevent polarization and stably detect radiations, via utilizing the formation reactions of a thallium metal and thallium bromide. However, since thallium is an acute toxic material, thallium should be handled by paying extreme attention, resulting in remarkable increase in the cost for producing a thallium bromide based detector.

From the viewpoints as mentioned above, the present invention is directed to the development of a thallium bromide based radiation detector which is produced without inserting thallium layers between a cathode and a thallium bromide crystal, and between an anode and the thallium bromide crystal, in the thallium bromide based radiation detector. Such a radiation detector allows lower priced radiation detection equipment to be provided. Herein, the radiation detection equipment is capable of preventing the cost from being increased by skipping the step of depositing the thallium layers, and also preventing polarization and realizing stable radiation detection. Further, the radiation detector allows a lower priced nuclear medicine diagnosis device using the radiation detection equipment to be provided.

As disclosed in the Non-patent Document 3, if the interval of reversing the polarities of the voltages applied to the cathode and the anode in the semiconductor radiation detector using thallium bromide for the semiconductor crystal is increased as 10 min or more, for example, as 2 hr, the polarization was incapable of being prevented and the stable radiation detection over a long time was incapable of being performed.

Here, if the cathode and the anode of the thallium based radiation detector are made of at least one kind of metal selected from gold, platinum and palladium, at the vicinity of the cathode, the following chemical reaction occurs.

$$Tl^+ + e^- \rightarrow Tl$$

On the contrary, at the vicinity of the anode, a complex formed by the coordination of a plurality of $Br^-$ ions with an atom of gold, platinum, or palladium, which partially prevents the accumulation of the $Br^-$ ions therein. However, since the reaction rate of forming the complex is slow, $Br^-$ ions may come to be accumulated if the radiation detector is operated over a long time.

Accordingly, it is needed to reverse the polarity of the bias voltage before $Br^-$ ions are accumulated at the vicinity of the anode, in order to prevent the polarization from occurring.

Taking the above mentioned aspect in consideration, the present inventors have found out that the polarization can be prevented and the energy resolution is not to be deteriorated, if the interval of reversing the polarity of the voltage is set in shorter than 10 min.

Following the above mentioned principle, the cathode and the anode of the semiconductor radiation detector have been formed by using at least one kind of metal selected from gold, platinum and palladium. Simultaneously, the DC power source has been constructed so that a voltage of accumulating positive charges in one of the electrodes of the capacitor and a voltage of accumulating negative charges in the other electrode of the capacitor are capable of being applied thereto via periodically reversing the polarity of each voltage per the interval shorter than 10 min.

This construction enables the present invention to provide radiation detection equipment at a lower cost with operation stability, and a nuclear medicine diagnosis device using the radiation detection equipment. Here, note in this construction, it is not needed to insert thallium layers between the cathode and the thallium bromide crystal, and between the anode and the thallium bromide crystal in a thallium bromide based radiation detector.

Further, the radiation detection equipment and the nuclear medicine diagnosis device mounting the radiation detection equipment in the present invention allow not only the operation stability of the equipment and the device to be secured and realize the lowering of the prices. Accordingly, these advantages may facilitate the equipment and the device to be widely spread, allowing the equipment and the device to be widely used and adopted in the fields of radiation detection equipment and a nuclear medicine diagnosis device.

DESCRIPTION OF REFERENCE NUMERALS 11, 21: Radiation Detection Equipment
31: Bed
32: Data Processor
33: Display
101: First DC Power Source
102: Second DC Power Source
103, 104, 302, 303: Protection Resistor
105, 304: First PhotoMOS Relay, PhotoMOS Relay
106, 305: Second PhotoMOS Relay, PhotoMOS Relay
107, 308: Control Unit for Switches
108, 309: First Constant Regulative Diode, Constant Regulative Diode
109, 310: Second Constant Regulative Diode, Constant Regulative Diode
110, 311: Smoothing Capacitor
111, 312: Semiconductor Crystal
112, 313: First Electrode
113, 314: Second Electrode
114, 315: Bleeder Resistor
115, 316: Coupling Capacitor
116, 317: Amplifier
117, 318: Control Unit for Polarity Integration
171, 371: Current Regulator
172, 372: Semiconductor Radiation Detector, Detector
206, 207: Detection Break Time
301: DC Power Source
306: Third PhotoMOS Relay, PhotoMOS Relay
307: Fourth PhotoMOS Relay, PhotoMOS Relay
600: SPECT Imaging Equipment (or Nuclear Medicine Diagnosis Device)
601A, 601B: Radiation Detection Block
602, 702: Detection Area
603, 703: Image Data Composing Device
606: Rotatable Support
611: Radiation Detection Unit
612: Circuit Board
613: Shade/Electromagnetic Shield
614: Collimator
615: Unit Support Member
700: PET Imaging Equipment (or Nuclear Medicine Diagnosis Device)
701: Imaging Equipment
D: Accumulation Unit
H: Subject
K: Collimator Partitioned Area
P: Printed Board

The invention claimed is:
1. Radiation detection equipment comprising:
a semiconductor radiation detector having a semiconductor crystal made of thallium bromide;
a capacitor of applying a voltage to the semiconductor radiation detector; and
at least one DC power source of respectively accumulating positive charges and negative charges in either of electrodes of the capacitor;
a current regulator of allowing a current to flow from the DC power source to the electrode of the capacitor;

at least two relays connected with a wire which connects the DC power source and the electrode of the capacitor;
an amplifier amplifying an output signal of the semiconductor radiation detector;
a first control unit controlling opening and closing of the relays; and
a second control unit for polarity integration of transmitting command signals comprised of "Apply positive bias", "Apply negative bias", "Reverse bias from positive to negative", and "Reverse bias from negative to positive" into the amplifier and the first control unit,
wherein a cathode and an anode of the semiconductor radiation detector are formed of at least one kind of a metal selected from gold, platinum and palladium, and
wherein the DC power source periodically reverses a voltage of accumulating positive charges and a voltage of accumulating negative charges in either of the electrodes of the capacitor per interval shorter than 10 min, thereby to apply the resulting voltage thereto.

2. The radiation detection equipment as described in claim 1, wherein the current regulator is constructed via connecting two constant regulative diodes in series so that polarities in constant-current characteristics of the constant regulative diodes are reversed with respect to other.

3. The radiation detection equipment as described in claim 1, wherein the at least two relays are photoMOS relays.

4. The radiation detection equipment as described in claim 1, wherein a cathode and an anode of the semiconductor radiation detector are formed of gold.

5. A nuclear medicine diagnosis device comprising:
a bed of supporting a subject;
a plurality of pieces of radiation detection equipment of placing the subject in a detection space; and
an image data composing device of creating an image by using data acquired through radiation detection signals which have been outputted from the plurality of pieces of the radiation detection equipment, wherein
the radiation detection equipment used in the nuclear medicine diagnosis device is selected from the radiation detection equipment as described in claim 1.

6. Radiation detection equipment comprising:
a semiconductor radiation detector having a semiconductor crystal made of thallium bromide;
a capacitor of applying a voltage to the semiconductor radiation detector;
at least two relays connected with a wire which connects the DC power source and the electrode of the capacitor;
a first DC power source of accumulating positive charges in either of the electrodes of the capacitor;
a second DC power source of accumulating negative charges in either of the electrodes of the capacitor; and
a current regulator of allowing a current to flow from the first DC power source or the second DC power source to the electrode of the capacitor,
wherein a cathode and an anode of the semiconductor radiation detector are formed of at least one kind of a metal selected from gold, platinum and palladium, and
wherein the first and second DC power sources periodically reverse a voltage of accumulating positive charges and a voltage of accumulating negative charges in either of the electrodes of the capacitor per interval shorter than 10 min, thereby to apply the resulting voltage thereto.

7. The radiation detection equipment as described in claim 6, wherein the current regulator is constructed via connecting two constant regulative diodes in series so that polarities in constant-current characteristics of the constant regulative diodes are reversed with respect to other.

8. The radiation detection equipment as described in claim 6, wherein the at least two relays are photoMOS relays.

9. The radiation detection equipment as described in claim 6, wherein a cathode and an anode of the semiconductor radiation detector are formed of gold.

10. A nuclear medicine diagnosis device comprising:
a bed of supporting a subject;
a plurality of pieces of radiation detection equipment of placing the subject in a detection space; and
an image data composing device of creating an image by using data acquired through radiation detection signals which have been outputted from the plurality of pieces of the radiation detection equipment, wherein
the radiation detection equipment used in the nuclear medicine diagnosis device is selected from the radiation detection equipment as described in claim 6.

11. The radiation detection equipment as described in claim 6, further comprising:
a first relay connected with a wire which connects the first DC power source and the electrode of the capacitor; and
a second relay connected with a wire which connects the second DC power source and the electrode of the capacitor.

12. The radiation detection equipment as described in claim 11,
wherein the at least two relays are photoMOS relays.

13. Radiation detection equipment comprising:
a semiconductor radiation detector having a semiconductor crystal made of thallium bromide;
a capacitor of applying a voltage to the semiconductor radiation detector;
at least one DC power source of respectively accumulating positive charges and negative charges in either of electrodes of the capacitor;
a current regulator of allowing a current to flow from the DC power source to the electrode of the capacitor;
a first relay connected with a wire which connects a positive electrode of the DC power source and the electrode of the capacitor;
a second relay connected with a wire which connects a negative electrode of the DC power source and the electrode of the capacitor;
a third relay connected with a wire which connects the positive electrode of the DC power source and ground; and
a fourth relay connected with a wire which connects the negative electrode of the DC power source and ground,
wherein a cathode and an anode of the semiconductor radiation detector are formed of at least one kind of a metal selected from gold, platinum and palladium, and
wherein the DC power source periodically reverses a voltage of accumulating positive charges and a voltage of accumulating negative charges in either of the electrodes of the capacitor per interval shorter than 10 min, thereby to apply the resulting voltage thereto.

14. The radiation detection equipment as described in claim 13, wherein the current regulator is constructed via connecting two constant regulative diodes in series so that polarities in constant-current characteristics of the constant regulative diodes are reversed with respect to other.

15. The radiation detection equipment as described in claim 13, wherein the first relay, the second relay, the third relay, and the fourth relay are photoMOS relays.

16. The radiation detection equipment as described in claim 13, wherein a cathode and an anode of the semiconductor radiation detector are formed of gold.

17. A nuclear medicine diagnosis device comprising:
a bed of supporting a subject;
a plurality of pieces of radiation detection equipment of placing the subject in a detection space; and
an image data composing device of creating an image by using data acquired through radiation detection signals which have been outputted from the plurality of pieces of the radiation detection equipment, wherein
the radiation detection equipment used in the nuclear medicine diagnosis device is selected from the radiation detection equipment as described in claim 13.

* * * * *